United States Patent [19]
Tritsch

[11] 3,937,221
[45] Feb. 10, 1976

[54] DISPOSABLE DIAPER WITH PERMANENTLY ATTACHED CLOSURE SYSTEM WITH A STRING GRIPPER

[75] Inventor: Ludwig Tritsch, Wilmette, Ill.

[73] Assignee: Johnson & Johnson, New Brunswick, N.J.

[22] Filed: July 18, 1974

[21] Appl. No.: 489,643

[52] U.S. Cl. ............................ 128/287; 128/284
[51] Int. Cl.² ...................................... A61F 13/16
[58] Field of Search ............... 128/284, 287, 290 R; 24/DIG. 11, 67 AR

[56] References Cited
UNITED STATES PATENTS

| | | | |
|---|---|---|---|
| 2,411,328 | 11/1946 | MacNab | 24/DIG. 11 |
| 2,714,889 | 8/1955 | Chambers | 128/287 |
| 2,902,734 | 8/1959 | Walters | 24/DIG. 11 |
| 3,011,471 | 12/1961 | Tay | 24/DIG. 11 |
| 3,612,055 | 10/1971 | Mesek | 128/287 |
| 3,620,217 | 11/1971 | Gellert | 128/284 |
| 3,776,232 | 12/1973 | Schaar | 128/287 |
| 3,848,594 | 11/1974 | Buell | 128/284 |
| 3,862,634 | 1/1975 | Small | 128/284 |

Primary Examiner—Aldrich F. Medbery

[57] ABSTRACT

A disposable diaper adhesive closure means is provided in which an adhesive tab used to apply the diaper about an infant is permanently attached to the diaper at one end, and the opposite free tacky end of the tab is folded over and releasably adhered to a central portion of the tab which is provided with a release coated surface. A string separator attached to the adhesive tab is interposed between the folded over free tacky end of the tab and the central portion leaving an exposed string end so that the exposed string end can be pulled to release the free end of the tab for use in fastening the diaper about a baby. The string remains attached to the tacky free end of the tab. This eliminates the need for disposal by the consumer of a cover strip or of any other part of the adhesive closure means when the diaper is applied.

6 Claims, 7 Drawing Figures

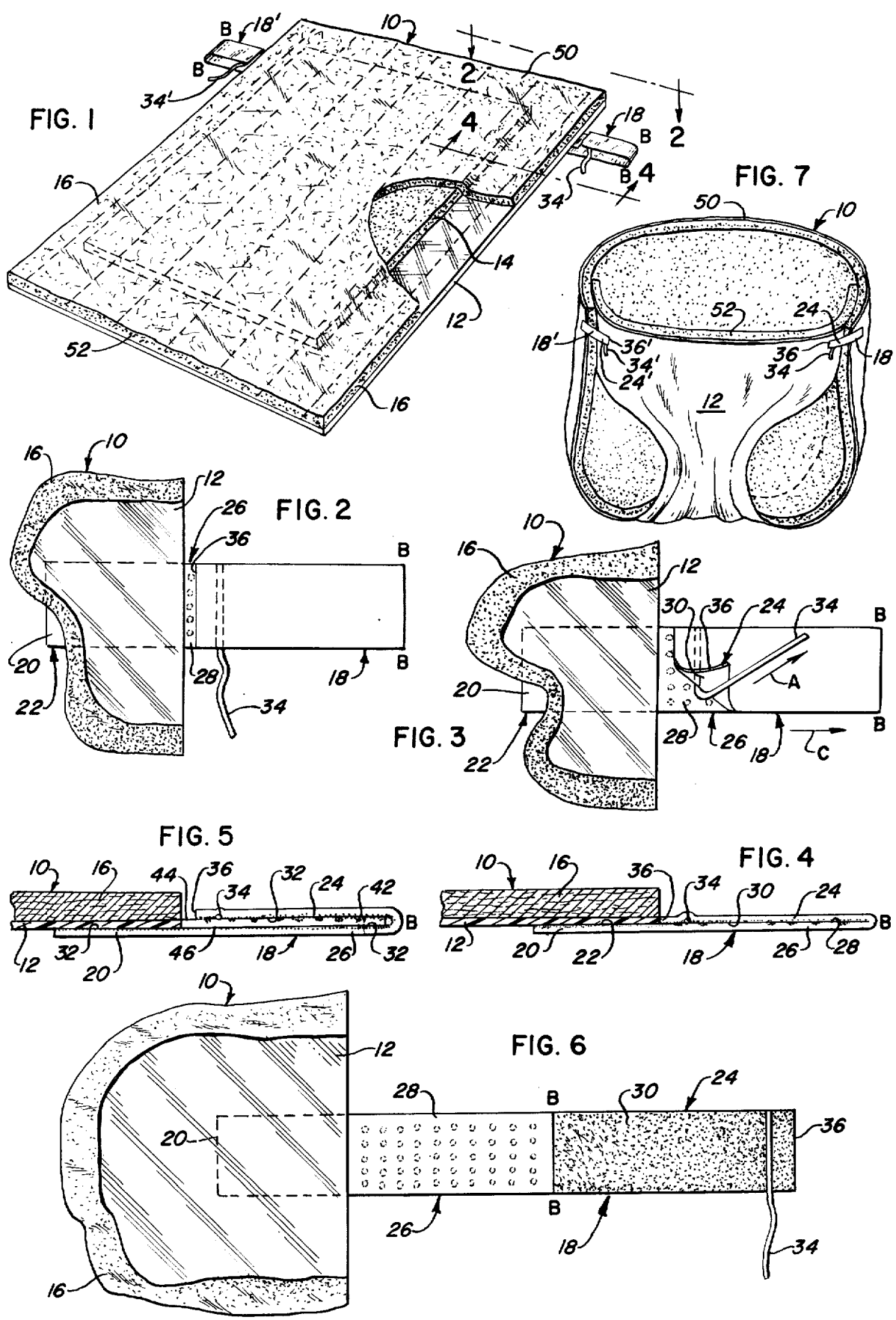

DISPOSABLE DIAPER WITH PERMANENTLY ATTACHED CLOSURE SYSTEM WITH A STRING GRIPPER

BACKGROUND OF THE INVENTION

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a facing material to be brought into contact with the infant's skin, an absorptive layer of high liquid-holding capacity and a moisture-impervious backing layer, generally made of a plastic film such as a polyethylene film. Typical disposable diaper structures are shown in Mesek et al. U.S. Pat. No. 3,612,055, and in Duncan et al. U.S. Pat. No. 3,180,335.

As may be seen from the above-cited patents, it has been desired to obviate the problems that are inherent in closure systems utilizing extraneous fasteners such as safety pins, snaps and zippers; and adhesive closure systems have therefore been found desirable.

One of the most convenient adhesive systems that has been developed to date is the system, shown in the above-cited patents, in which adhesive tabs are adhered to the backing sheet extending outwardly from opposite sides of the diaper at one end thereof, with the exposed areas of the adhesive strips having cover strips thereon that are readily separable from the adhesive tabs. Disposable diapers using an adhesive closure system of this general type have the disadvantage of requiring the consumer to dispose of the cover strips when they are separated from the adhesive strips. This is an inconvenience to the consumer who is placing the diaper on a baby.

As illustrative prior art adhesive system having cover strips permanently attached to the diaper is disclosed in Gellert U.S. Pat. No. 3,646,937. The Gellert arrangement has the disadvantage of having the release film on the inside of the diaper, where it can possibly come in contact with a baby's tender skin. Additional disadvantages are the complexities and expense which are added to the manufacturing process by requiring each adhesive closure to be manipulated on the front side, around the edge, and on to the back side of the diaper, instead of handling it on one side only. The closure system illustrated in the Gellert patent also makes it somewhat difficult to secure the diaper around a baby, inasmuch as it requires the use of two hands to peel back the releasable end of the adhesive tape.

SUMMARY OF THE INVENTION

In this invention, an adhesive tab for a diaper including an absorbent layer and a backing sheet on one side thereof comprises an elongated tape segment which has one of its ends permanently adhered to the diaper near a margin thereof, and has a tacky free end bearing an adhesive coating folded over upon a central portion of the tab which has a surface of limited adhesiveness so that this free end can be made available when needed with the aid of an interposed elongated separator element, such as a separating string, which is permanently attached to the free end. The separating string is positioned on the tab so that a portion of the separator element extends beyond the perimetric limits of the free end.

In one embodiment, the central portion of the tape segment forming the adhesive tab is coated with a release coating to provide the limited adhesiveness which permits ready release of the folded over free end. In a second embodiment, the central portion of the adhesive tab is provided with a tacky pressure sensitive coating which can be a continuation of the adhesive coating on the aforesaid tacky free end and which is covered with a permanently adhered cover strip having one face thereof adhered to the central portion of the tab, and having an opposite face which is coated with a release coating to provide the limited adhesiveness which permits ready release of the folded over free end. In both embodiments, the tacky free end portion of the adhesive tab is folded over into contact with the release coated surface along the central portion of the adhesive tab and is releasably adhered thereto. In both cases the folded over end portion of the adhesive tab can be separated from the release coated central portion by grasping the protruding end of the interposed string and pulling away, thereby lifting a portion of the tab to enable the tab to be grasped and pulled free of the release coated surface for use. A feature of this invention is that the tab can be separated from the release coated central portion upon which it is held ready for use by using only one hand, thus leaving the other hand free for other purposes.

In this invention, after the end of the tab is pulled free, the exposed release coated surface on the central portion advantageously faces the outside surface of the backing layer of the diaper and is out of contact with the baby's tender skin.

It is stressed that all parts of the adhesive closure means, including the string separator, remain permanently attached to the diaper, thereby obviating the need for the user to dispose of a cover strip or any other part of the closure means.

Additionally, when the release coating is formed directly on the central portion of the adhesive tab, the need for a separate cover strip is eliminated.

BRIEF DESCRIPTION OF THE DRAWINGS

This invention is ilustrated by reference to the drawings in which:

FIG. 1 is a perspective view, partly broken away of an open unfolded diaper in accordance with one embodiment of the invention;

FIG. 2 is an enlarged partial top plan view of the diaper of FIG. 1 taken along plane 2—2;

FIG. 3 is a partial top plan view like FIG. 2, illustrating the tab partially separated in preparation for use;

FIG. 4 is a partial cross section of the diaper of FIG. 1 taken along plane 4—4;

FIG. 5 is a partial cross section similar to FIG. 4,, illustrating an alternate embodiment of the invention.

FIG. 6 is a partial top plan view of the diaper of FIG. 2 illustrating an adhesive tab embodying the invention after the tab is extended and ready for use; and FIG. 7 is a perspective view on a reduced scale of the diaper of FIGS. 1, 2, 3, 4 and 6 in the configuration assumed after the diaper is placed on the infant.

DESCRIPTION OF THE PREFERRED EMBODIMENTS

While this invention is susceptible of embodiment in many different forms, there is shown in the drawings and will herein be described in detail preferred embodiments of the invention, with the understanding that the present disclosure is to be considered as an exemplification of the principles of the invention and is not intended to limit the invention to the embodiments illustrated. The scope of the invention will be pointed out in the appended claims.

Referring to the drawings, diaper assembly 10, when fully opened and laid out flat as illustrated in FIG. 1, comprises a lowermost moisture-impervious plastic backing sheet 12 which is generally rectangular in shape, and an overlying porous layer 16 of fibrous material which is substantially coextensive with the impervious sheet. Diaper 10 also preferably includes highly moisture-absorbent fibrous pad or batt 14, which is also rectangular in shape, but smaller than the facing and backing layers and is centrally disposed therebetween. Batt 14 may be formed in accordance with the teachings set forth in commonly assigned U.S. Pat. No. 3,612,055 to Mesek et al. Alternatively, a highly moisture-absorbent layer can be provided substantially coextensive with backing sheet 12 if desired.

Moisture-impervious sheet 12 may be formed of polyethylene having a thickness of approximately 0.001 inch. The sheet may be smooth or may be embossed to improve its drape and feel. Other suitable flexible moisture-impervious sheets may be used in accordance with the invention such as, for example, polyethylene terephthalate sheets having a thickness of about 0.0005 inch.

The present invention contemplates that several different types of facing layers may be used for the diaper. For example, the facing layer may be made up of a mixture of fibers consisting predominantly of inexpensive short cellulosic fibers such as wood pulp fibers or cotten linters, in amounts of about 75 to about 98 percent, the balance being textile length fibers such as rayon as described in U.S. Pat. No. 3,663,348 to Liloia et al.

Facing layers suitable for use in this invention have fabric weights in the range of 1 to 5 oz./yd.$^2$ and densities less than 0.15 gm./cc., generally in the range between 0.05 and 0.10 gm./cc. The dry strength of the facing layer, for a fabric having a weight of about 1.5 oz./yd.$^2$, is at least 0.15 lbs./in. of width in the machine direction and at least 0.10 lbs./in. of width in the cross direction. The fabrics have unusually good elongation, loft, softness, and drape characteristics in comparison to prior products incorporating any substantial amount of short fibers.

Facing layer 16 may also be an apertured nonwoven fabric formed, for example, in accordance with the teachings in commonly assigned U.S. Pat. Nos. 2,862,251; 3,081,514, and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well understood by those skilled in the art. A suitable binder may be utilized to help retain the fibers in their rearranged locations, as is also well understood by those skilled in the art. The fabric can be made of naturally occurring fibers, synthetic fibers or blends thereof. Typical facing layers made of a polyester material may have a weight of ¾ oz.yd.$^2$.

It should also be understood that the facing layer may be formed of a nonapertured material, such as a nonwoven isotropic web, sponge, or the like. In all of the aforementioned facings, the materials should be relatively hydrophobic so as to retard wicking within the facing layer.

As can be seen in FIG. 1, identical adhesive tabs 18 and 18' made from polyethylene tape stock, polypropylene tape stock, or the like, are secured at one end of the diaper and protrude from the sides thereof, these tabs being shown in their folded over storage position. As noted hereinbefore, tabs 18 and 18' are unfolded for use in securing diaper 10 about the baby, and the completed diaper is pictured in FIG. 7 where tabs 18 and 18' are shown in use holding the ends of the diaper together.

Referring more particularly to FIGS. 2 and 4, the construction of tab 18 is shown in greater detail. It should first be noted that tab 18 has three portions along its length. End portion 20 of tab 18 is permanently adhered to plastic backing sheet 12 of diaper 10 at a marginal location thereon. Tab 18 also is provided with free end 24 and central portion 26 which is situated between adhered end portion 20 and free end 24.

This invention contemplates various embodiments by which central portion 26 of tab 18 is provided with a release coated surface to which free end portion 24 of tab 18 is releasably adhered. In one embodiment, which is best illustrated in FIGS. 3 and 4, adhesive tab 18 is provided with pressure sensitive adhesive coating 22 on end 20 which is permanently attached to the diaper, and with pressure sensitive adhesive coating 20 on free end 24. Central portion 26 is provided with a release coating such as a silicone rubber coating, or the like, which presents release surface 28 between tacky surface 22 on end 20 and tacky surface 30 on free end 24.

In a further embodiment, illustrated in FIG. 5, the entire length of tab 18 is provided with tacky surface 32. In this embodiment, central portion 26 of tab 18 is covered with permanently attached cover strip 42 having release coated face 44. Opposite face 46 of cover strip 42 is adhered to surface 32 in the region of central portion 26 of tab 18.

With either embodiment the adhesive coating on free end 24 is contiguous to the release coating on central portion 26 and tab 18 is folded over upon itself about line B—B such that substantially the entire tacky surface of end portion 24 is releasably attached to central portion 26 of tab 18.

In either embodiment separator string 34 is provided between face end 24 and central portion 26. As illustrated in FIGS. 2 and 3, short length of separator string 34, interposed between the folded over free end 24 and central portion 26 of tab 18, is adhesively held on tacky surface 30. Separator string 34 is positioned transversely on tacky surface 30 near narrow edge 36, usually about one-eighth to about one-fourth inch from narrow edge 36 of tab 18, and protrudes beyond tab 18 for about one-fourth to about one width thereof. For example, when tab 18 is about 1 inch wide, string 34 protrudes about one-fourth to about 1 inch beyond the side margin of tab 18 so that the protruding portion of string 34 can be grasped by user. String 34 remains permanently adhered or otherwise affixed to tab 18.

FIGS. 2, 3 and 6 sequentially illustrate use of separator string 34 to separate the folded-over free end 24 of tab 18 from central portion 26 to which it is releasably adhered. Separation is effected by grasping the protruding portion of string 34 between one's forefinger and thumb and peeling end portion 24 away from central portion 26 by pulling string 34 in the direction indicated by arrow A, thereby lifting up one corner of the folded-over end portion 24. This enables the user to grasp free end 24 of tab 18 near end border 36 of tab 18 and pull in the direction indicated by arrow C. FIG. 6 illustrates the embodiment of FIGS. 1–4 in its fully extended position after end 24 is totally separated from central portion 26 and presents an adhesive surface facing in the same direction as layer 16. The diaper can then be secured about the infant.

As illustrated in FIGS. 2, 3, and 5, it is desirable to have central portion 26 slightly longer than end section 24 to thereby increase tolerances during manufacture, and to more easily enable tacky surface 30 of end section 24 to be covered by the release coated portion 26 and releasably adhered thereto. Materials such as thread, nylon, or other plastic monofilaments, are suitable for use as separator means 34.

After end portion 24 of tab 18 is totally separated from the central portion 26 and the diaper is applied to the infant, all components of the adhesive closure means of this invention remain permanently attached to the diaper, thereby obviating the need for the user to dispose of a release strip or any other component of the closure means. Additionally, after end portion 24 of tab 18 is totally separated from the central portion 26 and the diaper is applied to the infant, the exposed release coated surface 28 in FIG. 4 or 44 in FIG. 5 of central portion 26 faces the outer surface of the diaper, where it will not come in contact with a baby's tender skin. Another feature is that each adhesive tab can be readied for application of the diaper to the infant by using only one hand, thus leaving the user's other hand free for other purposes. A further advantage of the embodiment of this invention illustrated in FIGS. 1–4 and 6 is the elimination of the need for any release strip. This is accomplished by having central portion 26 of the adhesive tab 18 provided with release coated surface 28 to which tacky surface 30 of free end 24 of tab 18 is releasably adhered.

Suitable pressure-sensitive adhesives for the present purposes are known in the art and possess good tack, good cohesive strength, good moisture resistance and good resistance to aging. Illustrative of such adhesive compositions are mixtures of natural or synthetic rubber with zinc oxide and various resins, natural or synthetic rubber or resin latices, tacky acrylic polymers or copolymers, and the like.

As illustrated in FIGS. 1 and 7, diaper 10 is applied to the infant by positioning the ends 50 and 52 of the diaper around the waist of the infant with the intermediate portion of the diaper being disposed in the infant's crotch. Free end portion 24 of tabs 18 and 18' is separated from the respective tab central portions, and diaper ends 50 and 52 are pulled into tight fitting engagement with the infant's waist. The exposed portion of tacky surface 30 (in the embodiment in FIG. 4) or tacky surface 32 (in the embodiment in FIG. 5) along ends 24 and 24' of respective tabs 18 and 18' are then pressed against the adjacent portions of plastic backing sheet 12 to secure the diaper on the infant. The final form assumed by diaper 10 is shown in perspective on a reduced scale in FIG. 7, and diaper 10 is held in this position by the adhesive closure system of the present invention.

The foregoing description and the drawing are illustrative but are not to be taken as limiting. Still other variations and modifications are possible without departing from the spirit and scope of this invention.

What is claimed is:

1. An adhesive tab means for a disposable diaper having an absorbent layer and a moisture-impervious backing sheet at one side thereof which comprises an elongated tape segment permanently attached at one end to said backing sheet at a marginal location thereon and providing a central portion and a free end; a release coating on a surface of said central portion which faces in the same direction as said absorbent layer; an adhesive coating on said free end contiguous to said release coating; and an elongated separator means attached to said free end and extending substantially transversely across and beyond the perimetric limits of said free end; said free end being folded over upon said central portion and being releasably adhered to said release coating, and a portion of said elongated separator means protruding beyond said free end and being adapted for gripping to peel said free end away from said central portion for fastening said diaper about a baby.

2. The adhesive tab means as set forth in claim 1 wherein said elongated separator means is a short length of string.

3. The adhesive tab means as set forth in claim 2 wherein the string is positioned near the narrow edge of the folded-over free end of the tab.

4. The adhesive tab means as set forth in claim 2 wherein the string extends beyond the tab for about one-fourth to about one width of the tab.

5. The adhesive tab means as set forth in claim 1 wherein said elongated separator means is interposed between said folded-over free end and said central portion and is held on said free end by said adhesive coating.

6. In combination with a disposable diaper having an absorbent layer and a moisture-impervious backing sheet substantially coextensive therewith, the improvement comprising: an adhesive tab means which is an elongated tape segment having one end permanently adhered to said backing sheet at a marginal location thereon and providing a central portion and a free end, having a release coating on a surface of said central portion facing in the same direction as said absorbent layer, having an adhesive coating on said free end contiguous to said release coating, and having an elongated separator means attached to said free end and extending substantially transversely across and beyond the perimetric limits of said free end; said free end being folded over upon said central portion and being releasably adhered to said release coating, and a portion of said elongated separator means protruding beyond said free end and being adapted for gripping to peel said free end away from said central portion for fastening said diaper about a baby.

* * * * *

UNITED STATES PATENT AND TRADEMARK OFFICE
CERTIFICATE OF CORRECTION

PATENT NO. : 3,937,221

DATED : February 10, 1976

INVENTOR(S) : Tritsch, Ludwig

It is certified that error appears in the above-identified patent and that said Letters Patent are hereby corrected as shown below:

In Column 4, line 32, the word "coating 20" should read --- coating 30 ---.

Signed and Sealed this fourth Day of May 1976

[SEAL]

Attest:

RUTH C. MASON
*Attesting Officer*

C. MARSHALL DANN
*Commissioner of Patents and Trademarks*